United States Patent [19]

Schouteeten et al.

[11] 4,408,070

[45] Oct. 4, 1983

[54] PURE CRYSTALLINE RACEMIC SODIUM PARAHYDROXYMANDELATE, PROCESS FOR ITS PREPARATION AND USES THEREOF

[76] Inventors: Alain Schouteeten, 17, rue de Normandie, Ezanville, Val d'Oise; Yani Christidis, 12, rue de Constantinople, Paris 8eme, Seine, both of France

[21] Appl. No.: 284,835

[22] Filed: Jul. 20, 1981

Related U.S. Application Data

[63] Continuation of Ser. No. 96,597, Nov. 21, 1979, abandoned.

[30] Foreign Application Priority Data

Jun. 15, 1979 [FR] France ............................ 79 15392

[51] Int. Cl.³ ........................................ C07C 65/135
[52] U.S. Cl. ............................. 562/470; 568/432; 568/435; 568/442
[58] Field of Search ............... 568/431, 432, 435, 442; 562/470

[56] References Cited

U.S. PATENT DOCUMENTS

| | | | |
|---|---|---|---|
| 2,062,205 | 11/1936 | Boedecker et al. | 568/435 |
| 4,163,759 | 8/1979 | Bauer | 260/600 |
| 4,165,341 | 8/1979 | Umemura | 260/600 |
| 4,198,523 | 4/1980 | Copeland | 562/470 |
| 4,346,238 | 8/1982 | Schouteeten | 568/432 |

FOREIGN PATENT DOCUMENTS 751687 6/1933 France .............................. 568/435

OTHER PUBLICATIONS

Krings, Zeitschrift fur Anorganische Chemie, Band 255, 294 (1948).
Aloy, Bull. Soc. Chim France, 4,392 (1912).
Ladengburg, J. Am. Chem. Soc., 58, 1292 (1936).
Ellinger, Zeitschrift fur Physioqische Chemie, 65 402 (1910).
Fatiadi, Jour. of Research of the Nat. Bur. of Stand.-A 78A 411 (1974).
Weissberger, Separation and Purification, Part I, p. 473 (1956).
Wiberg, Laboratory Techninque in Organic Chemistry pp. 99–106 (1960).

Primary Examiner—Robert Gerstl
Attorney, Agent, or Firm—Karl W. Flocks; Sheridan Neimark

[57] ABSTRACT

Pure crystalline racemic sodium parahydroxymandelate free from any ions of chloride, acetate, formate and sulfate group, is manufactured by condensing in water, in the presence of sodium hydroxide at a temperature between 30° and 100° C., glyoxylic acid or sodium glyoxylate with an excess of phenol, concentrating it hot, until the start of crystallization of the solution thus obtained after neutralization and removal of the unconverted phenol either by steam distillation, or by extraction with a water-immiscible organic solvent. The resulting suspension obtained is cooled, drained after some hours of standing at a temperature close to 5° C., and the resulting precipitate recovered by washing it with iced water followed by drying to constant weight. The product is useful for the manufacture of crystalline sodium paraformylphenolate.

3 Claims, No Drawings

PURE CRYSTALLINE RACEMIC SODIUM PARAHYDROXYMANDELATE, PROCESS FOR ITS PREPARATION AND USES THEREOF

This is a continuation of application Ser. No. 093,597, filed Nov. 21, 1979, abandoned.

BACKGROUND OF THE INVENTION

1. Field of the Invention

The present invention relates to pure crystalline racemic sodium parahydroxymandelate, the process for its preparation and its uses. It relates more particularly, by way of novel industrial product, to anhydrous crystalline racemic sodium parahydroxymandelate or racemic sodium parahydroxymandelate crystallized with one molecule of water free from any ions of chloride, acetate, formate, sulfate group and the like.

2. Description fo the Prior Art

Certain salts of racemic parahydroxymandelic acid are described in the literature. Calcium parahydroxymandelate crystallized with 5.5 molecules of water and cinchonine parahydroxymandelate were isolated by A. ELLINGER et al., Z. Physiol. Chem., 65, 402–13, 1910. Intermediately, in the course of certain preparations of racemic parahydroxymandelic acid, either sodium parahydroxymandelate, or disodium 4-oxidomandelate have sometimes been obtained or used in aqueous sodium solution as, for example, in the alkaline hydrolysis of 4-dibenzoyloxy, $\alpha$phenylacetamide according to J. ALOY et al., Bull. Soc. chim. France, 4, 11, 389–93 (1912) or of parahydroxyphenyltrichloromethylcarbinol according to H. HAAKH et al., Austrain Patent AT 141 159 or of ethyl parahydroxymandelate according to K. LANDENBURG et at., J. Amer. Chem. Soc. 58, 1292–94 (1936) or in the condensation of glyoxylic acid with phenol according to French Patent Application No. 78 31.123 of Nov. 3, 1978.

More recently solid monohydrate sodium prahydroxymandelate containing sodium chloride (about 10% by weight) has been isolated from its aqueous preparing solution from glyoxylic acid and phenol with salting by sodium chloride (see Belgium Pat. No. 867.287, Chemical Abstracts, 1979, 90, 870 67 g).

Moreover referring to U.S. Pat. No. 4,154,757, anhydrous sodium parahydroxymandelate having a purity of 99% only and containing 1% by weight of sodium chloride, is obtained from the monohydrate form by azeotropic removal of the water using toluene or xylene as azeotroping solvent.

However, insofar as is known, pure crystallized racemic sodium parahydroxymandelate (i.e. not containing other anions such as chloride, acetate, formate, or sulfate) in anhydrous form or with one molecule of water has never been either isolated or described. Such a product free of chloride ions is suitable for preparing parahydroxybenzaldehyde by degradative oxidizing decarboxylation in a stainless steel reactor.

GENERAL DESCRIPTION OF THE INVENTION

According to the invention, crystalline racemic sodium parahydroxymandelate can be prepared, by condensing in water of glyoxylic acid or of sodium glyoxylate with an excess of phenol, desirably to 2 to 3 mols of phenol per mol of glyoxylic acid, in the presence of sodium hydroxide, desirably an amount of 2 to 3 mols per mol of glyoxylic acid, at a temperature between 30° and 100° C., desirably between 70° and 80° C., hot concentrating until the start of crystallization of the solution thus obtained after neutralization with an acid such as acetic acid and removal of the unconverted phenol either by steam distillation or by extraction with a water-immiscible organic solvent, cooling the resulting suspension obtained, draining after some hours of standing at a temperature close to 5° C., recovering the resulting precipitate and washing it with iced water followed by drying at 40° C. to constant weight. Pure racemic sodium parahydroxymandelate crystallized with one molecule of water is thus obtained. The latter is in the form of colorless prisms, nonhygroscopic, insoluble in ether, benzene, toluene and cyclohexane, and soluble in water, methanol and ethanol. It does not contain any impurities such as chloride, acetate, formate, sulfate and the like ions.

It does not lose its water of crystallization by drying at 60° C. to constant weight, but dried at 110° C., it supplies quantitatively pure anhydrous crystalline racemic sodium parahydroxymandelate which has a solubility in water at 20° C. of 19.0 g per 100 g. Such an aqueous solution acidified to pH=1 or treated with cation exchange resin with sulphonic groups, leads to the pure racemic parahydroxymandelic acid.

The invention also relates to the use of the crystalline racemic sodium parahydroxymandelate in the industrial manufacture of crystalline sodium paraformylphenolate.

It is known that the cleavage of mandelic aids gives rise to aromatic aldehydes (U.S. Pat. No. 2,062,205). Moreover in French Patent application No. 79 12.173 there is claimed a process for the preparation of crystalline sodium paraformylphenolate from phenol and glyoxylic acid. Now, it has been discovered that crystalline racemic sodium parahydroxymandelate enables crystalline sodium paraformylphenolate to be obtained with excellent yields.

According to the invention, the process consists of subjecting a sodic aqueous solution of crystalline racemic sodium parahydroxymandelate to catalytic decarboxylating oxidizing degradation and then, after removal of the catalyst, of concentrating the solution obtained until the start of crystallization while hot, then draining the cooled suspension and finally drying the precipitate collected to constant weight under vacuum at 20° C. Sodium paraformylphenolate crystallized with two molecules of water is thus isolated. If the precipitate collected is dried to constant weight under vacuum at 100° C., anhydrous crystalline sodium paraformylphenolate is isolated.

More precisely, the process consists of subjecting an aqueous solution containing from 2 to 25% of sodium parahydroxymandelate crystallized with one molecule of water and from 1 to 25% of sodium hydroxide to catalytic decarboxylating oxidizing degradation at a temperature $\leq 140°$ C. and at a pressure of oxygen $\leq 6$ bars in the presence of cupric salts alone or in admixture with other salts of metals of Group VIII of the MENDELEIEV table for 0.1 to 5 hours, of removing the catalyst by filtration, of then concentrating the filtrate hot until the start of crystallization, then draining and washing with a little iced water the precipitate obtained after leaving the suspension for some hours at a temperature close to $+5°$ C. and finally drying to constant weight under vacuum at 20° C., in the presence of potassium hydroxide in pellets, the sodium paraformylphenolate crystallized with two molecules of water, thus obtained.

DESCRIPTION OF PREFERRED EMBODIMENTS

The following examples are given purely by way of non-limiting illustration of the invention.

EXAMPLE 1

A solution of 296 g (2 moles) of 50% glyoxylic acid in water, 564 g (6 moles) of phenol and 160 g (4 moles) of sodium hydroxide in pellets in 3600 g of water is heated for 30 minutes to 82±2° C., with stirring and under a nitrogen atmosphere. Then, after cooling, the reaction solution is brought to pH=6.7±0.2 with acetic acid, then the unconverted phenol is extracted with 1,2-dichloroethane. Thus, after removal of the extraction solvent, 376 g (4 moles) of phenol are isolated. The aqueous solution is then concentrated hot under vacuum to 30% of its weight and then left to crystallize for some hours towards 5±2° C. Finally, the crystalline precipitate formed is drained and washed with ice water and then dried on a fluidized bed at 40° C. to constant weight. 254 g (1.22 mole) of sodium parahydroxymandelate crystallized with one molecule of water is thus obtained in the form of colorless prisms, namely a yield of 61% of the theoretical calculated with respect to the glyoxylic acid used.

| MW = 208.15 | Microanalysis $C_8H_9NaO_5$ | | |
|---|---|---|---|
| | C % | H % | H₂O %* |
| calculated | 46.16 | 4.36 | 8.65 |
| found | 46.1 | 4.5 | 8.9 | sulphuric ash 34.0% (theoretical 34.2%)
*Determined by the method of K. FISCHER.

Search of $Cl^-$ ions by the silver nitrate test: negative.
Search of $SO_4^{31-}$ ions by barium chloride test: negative.

PHYSICAL ANALYSES

Acidimetry carboxylate function 4.83±0.05 meq/g
namely 100±1% of theory
phenol function 4.77±0.05 meq/g
namely 99.3±1% of theory
infrared (KBr)-spectrum in agreement with the proposed structure.
NMR of the proton at 60 MHz in deuterated DMSO (internal reference TMS).

| 3.9 ppm | 3H | m | H₂O and OH benzylic |
|---|---|---|---|
| 4.42 ppm | 1H | s | CH benzylic |
| 6.8 ppm | 4H | m | aromatic. |

The pure racemic parahydroxymandelate crystallized with one molecule of water, dried at 110° C., supplies pure anhydrous crystalline racemic parahydroxymandelate.

This product is in the form of colorless prisms, very soluble in water, methanol and ethanol, insoluble in benzene, ether and toluene.

EXAMPLE 2

Procedure is as in Example 1, but at the end of the reaction, after neutralization of the reaction solution with acetic acid, this solution is concentrated hot at ambient pressure to about one-third of its weight and then the azeotropic distillation of the phenol is continued until the end of the entrainment keeping the volume constant in the boiler by the addition either of water, or of steam. After complete removal of the unconverted phenol, the reaction medium is left to crystallize for some hours towards 5±2° C., then the crystalline precipitate obtained is drained and washed with ice water and finally it is dried on a fluidized bed at 40° C. to constant weight. 254.3 g (1.22 mole) of pure racemic sodium parahydroxymandelate crystallized with one molecule of water is thus obtained in the form of colorless prisms, namely a yield of 61% of the theoretical calculated from the glyoxylic acid utilized.

EXAMPLE 3

104 g (0.5 mole) of racemic sodium parahydroxymandelate crystallized with one molecule of water, 1 g of cupric sulphate pentahydrate, 1 g of coblt (II) acetate tetrahydrate in 1350 g of a 6.8% by weight aqueous solution of sodium hydroxide is heated for four hours at 120° C. in an autoclave in an oxygen atmosphere at a pressure of 4 bars. After cooling, the catalyst is filtered off, then the filtrate is concentrated hot under vacuum to one-third of its weight, it is then left to crystallize towards 5±2° C. for some hours. Finally, the crystalline precipitate obtained is drained and washed with ice water. It is dried under vacuum at 20° C. to constant weight in the presence of pelletized potassium hydroxide. 77.5 g (0.43 mole) of sodium paraformylphenolate crystallized with 2 molecules of water in the form of colorless platelets having a melting point of 122±3° C. with decomposition (literature M.P.=122±3° C., French Patent application No. 79 12.173) is thus isolated, namely a yield of 86% of the theoretical calculated from the sodium parahydroxymandelate crystallized with one molecule of water utilized. If the drying is carried out at 100° C. under vacuum to constant weight, anhydrous crystalline sodium paraformylphenolate is obtained with the same yield.

It is self-evident that the present invention has only been described purely by way of non-limiting illustration and that any modification could be introduced therein without departing from its scope as defined in the appended claims.

We claim:

1. A process for the preparation of crystalline sodium paraformylphenolate comprising
   subjecting crystalline racemic sodium parahydroxymandelate in aqueous solution to catalytic decarboxylating oxidizing degradation hot, under oxygen pressure, and in the presence of sodium hydroxide,
   said crystalline racemic sodium parahydroxymandelate being prepared, as a preliminary operation, in pure crystalline form according to the steps consisting essentially of
   condensing, over a period of approximately one-half hour, glyoxylic acid or sodium glyoxylate with an excess of 2 to 3 mols of phenol, in water, and in the presence of 2 to 3 mols of sodium hydroxide per mol of glyoxylic acid, at a temperatue between 70° and 100° C.;
   neutralizing the resultant reaction medium, and removing unconverted phenol either by steam distillation or by extraction with a water-immiscible organic solvent;
   concentrating the resultant reaction medium until the start of the formation of crystals, and cooling the resultant crystals; and
   drying said crystals to constant weight at approximately 40° C. to provide pure sodium parahydroxymandelate crystallized with one molecule of water and substantially free of any ions of chloride, acetate, formate or sulphate, or drying said crystals at approximately 110° C. to provide pure anhydrous crystalline sodium parahydroxymandelate substantially free of any ions of chloride, acetate, formate or sulphate.

2. A process for the manufacture of pure crystalline racemic sodium parahydroxymandelate either with one molecule of water or in anhydrous form and substantially free of any ions of chloride, acetate, formate and sulphate, consisting essentially of the steps of condensing, over a period of approximately one-half hour, glyoxylic acid or sodium glyoxylate with an excess of 2 to 3 mols of phenol, in water, and in the presence of 2 to 3 mols of sodium hydroxide per mol of glyoxylic acid, at a temperature between 70° and 100° C.;

neutralizing the resultant reaction medium, and removing unconverted phenol either by steam distillation or by extraction with water-immiscible organic solvent;

concentrating the resultant reaction medium until the start of the formation of crystals, and cooling the resultant crystals; and drying said crystals to constant weight at approximately 40° C. to provide pure sodium parahydroxymandelate crystallized with one molecule of water and substantially free of any ions of chloride, acetate, formate or sulphate, or drying said crystals at approximately 110° C. to provide pure anhydrous crystalline sodium parahydroxymandelate substantially free of any ions of chloride, acetate, formate or sulphate.

3. A process according to claim 2, wherein the neutralization of the resultant reaction medium is carried out with acetic acid.

* * * * *

UNITED STATES PATENT AND TRADEMARK OFFICE
CERTIFICATE OF CORRECTION

PATENT NO.  :  4,408,070
DATED       :  October 4, 1983
INVENTOR(S) :  Alain Schouteeten and Yani Christidis It is certified that error appears in the above—identified patent and that said Letters Patent is hereby corrected as shown below:

On the face of the patent, insert the information concerning the assignee as follows:

-- Assignee: Societe Francaise Hoechst, France --

Signed and Sealed this

Twentieth Day of August 1985

[SEAL]

Attest:

DONALD J. QUIGG

Attesting Officer

Acting Commissioner of Patents and Trademarks